United States Patent [19]
Hasson

[11] Patent Number: 4,944,741
[45] Date of Patent: Jul. 31, 1990

[54] LAPROSCOPIC INSTRUMENT WITH PIVOTABLE SUPPORT ARM

[76] Inventor: Harrith M. Hasson, 2043 N. Sedgwick, Chicago, Ill. 60614

[21] Appl. No.: 281,626

[22] Filed: Dec. 9, 1988

[51] Int. Cl.[5] ............................................. A61B 17/28
[52] U.S. Cl. .................................... 606/206; 606/207
[58] Field of Search .............. 128/354, 321; 294/99.2, 294/100; 81/424; 606/205, 206, 207, 210, 148, 151; 433/159

[56] References Cited

U.S. PATENT DOCUMENTS

| | | | |
|---|---|---|---|
| 4,393,872 | 7/1983 | Reznik et al. | 128/321 X |
| 4,744,363 | 5/1988 | Hasson | 128/321 |
| 4,827,930 | 5/1989 | Kees | 128/346 X |

Primary Examiner—Michael H. Thaler
Attorney, Agent, or Firm—Wood, Phillips, Mason, Recktenwald & Vansanten

[57] ABSTRACT

A surgical instrument having an elongated stem with first and second jaws selectively movable towards and away from each other between open and closed positions, an arm with an elongate edge mounted to one of the jaws for movement between (a) a first, entry position wherein the length of the edge is aligned lengthwise of the elongate stem and (b) a second, support position wherein the length of the edge is transverse to the position that the edge assumes with the arm in its first position, and structure for manually moving the arm selectively between its first and second positions.

19 Claims, 1 Drawing Sheet

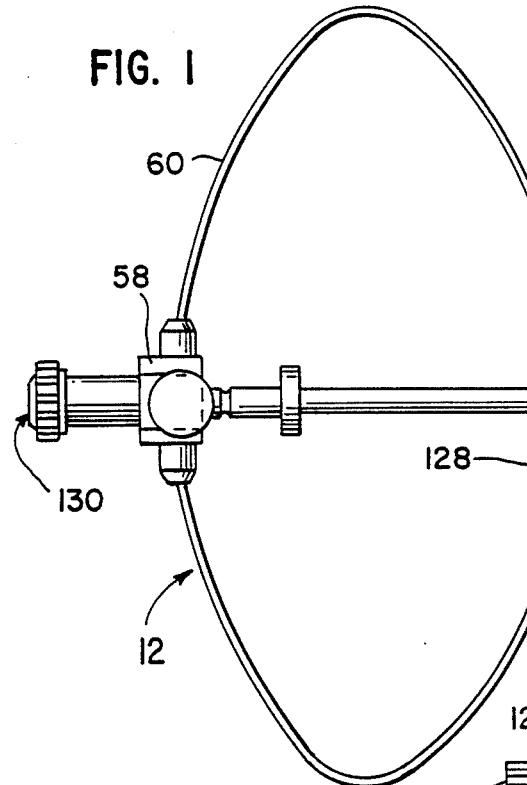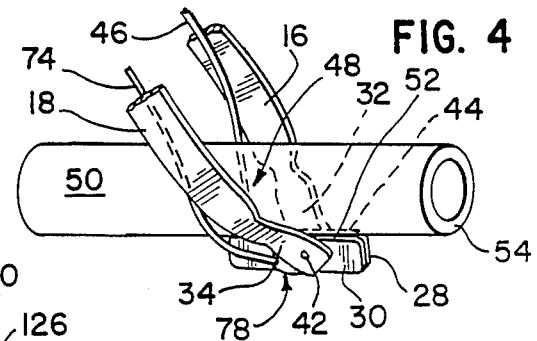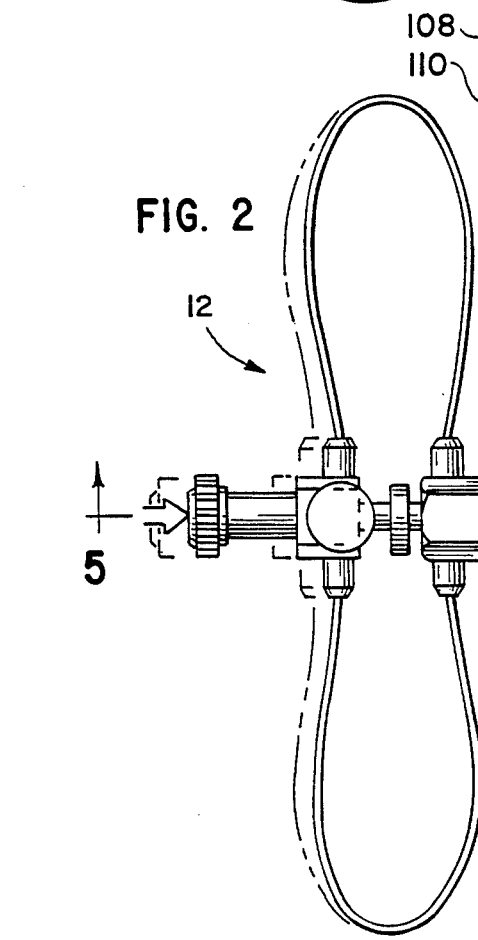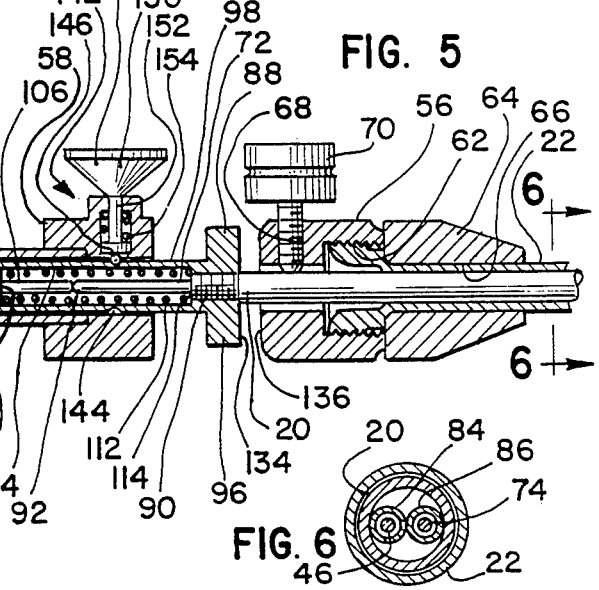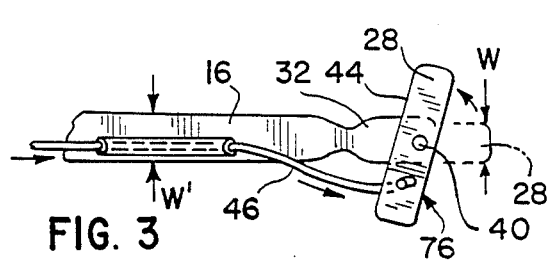

LAPROSCOPIC INSTRUMENT WITH PIVOTABLE SUPPORT ARM

BACKGROUND OF THE INVENTION

1. Field of the Invention

This invention relates to surgical instruments, as used for the performance of laproscopic surgery, and, more particularly, to an instrument with an elongate support arm that is pivotable from a location remote from the arm.

2. Background Art

To perform laproscopic surgery, instruments are inserted through discrete openings in the abdominal wall, thereby obviating the need for long incisions with their attendant complications to the patient. To provide the instrument opening, a "nail" with a surrounding sheath is forced through the abdominal wall. With the nail removed, the sheath provides a conduit for the passage of surgical instruments, which may be lasers, forceps, fiber optic cameras, etc. A plurality of instruments may be utilized at the same time through a corresponding number of abdominal openings.

One problem that has been particularly vexatious is the problem of manipulating vessels/tubes or stents during a laproscopic procedure. For example, reconnection of the fallopian tubes after a tubal ligation requires that the separate tube parts be aligned against each other and stabilized for suturing. The insertion of a small tube into the fimbriated end of the fallopian tube is yet another example. In this procedure, useful for Gamete Intro Fallopian Transfer (GIFT), tubal inseminations and the like; the fallopian tube is to be stabilized so as to permit feeding a smaller tube through its abdominal end. At the same time, the smaller tube is best held broadly along its axis, rather than at one point, to facilitate its introduction into the fallopian tube. The sheath defining the abdominal through passage normally has a very small diameter which limits the size of the jaws on instruments normally used to grasp such tubes during such procedures. It is difficult to maintain the alignment of such tubes with conventional laproscopic instruments having small jaws. Heretofore, the only solution to this problem has been to significantly increase the size of the sheath to permit passage of jaws with a more substantial working surface area. However, this solution is undesirable because the larger abdominal opening results in increased healing time, larger incisions and less appealing scars.

Summary of the Invention

The present invention is specifically directed to overcoming the above enumerated problems in a novel and simple manner.

The present invention comprehends a surgical instrument having an elongate stem with first and second jaws selectively movable towards and away from each other between open and closed positions, an arm with an elongate edge mounted to one of the jaws for movement between (a) a first, entry position wherein the length of the edge is aligned lengthwise of the elongate stem and (b) a second, support position wherein the length of the edge is transverse to the position that the edge assumes with the arm in its first position, and structure for manually moving the arm selectively between its first and second positions.

With the inventive structure, it is possible to extend the stem with the associated jaws and arm through a relatively small sheath and thereafter reposition the arm for the performance of a surgical procedure. The edge defines a support surface as for tubes/vessels or stents. After the surgery is completed, the arm can be reset to its entry position so that the instrument has a compact profile to facilitate its withdrawal from the sheath.

In a preferred form, there is an arm associated with each jaw and the jaws are bowed so as to define an opening for the passage of a tube/vessel, which can be supported cooperatively by the elongate edges defined by the arms. The jaws are normally biased away from each other to their open position. The stem is surrounded by a sleeve, which is slidable lengthwise relative to the stem into surrounding relationship with the jaws, thereby squeezing the jaws towards each other and their closed position. The stem is normally biased to situate the sleeve in surrounding relationship with the jaws so that the jaws are urged against their normal bias to a closed position. Structure is also provided to fix the relative lengthwise positions of the sleeve and stem so that the jaws can be maintained fixedly in each of the open and closed positions.

First and second rods are provided within the sleeve and operable to move the arms between their first and second positions.

Structure is also provided to releasably maintain the arms in each of their first and second positions. Preferably, a detent-type arrangement is provided to accomplish this end.

In one form of the invention, a sleeve block and separate pusher block are provided. The sleeve block is fixed to the sleeve and the pusher block is used to shift the stem and rods relative to the sleeve.

To facilitate operation of the instrument, a pair of finger grips are provided on the sleeve block and can be used to hold the instrument as a conventional-style syringe. The pusher block can then be shifted relative to the sleeve block by the thumb of a user.

Other objects and advantages of the invention will be apparent from the following detailed description, the drawings and the appended claims.

Brief Description of the Drawings

FIG. 1 is a plan view of a surgical instrument according to the present invention with jaws associated therewith shown in a closed position;

FIG. 2 is a plan view of the device with the jaws in an open position;

FIG. 3 is an enlarged section view of the jaws taken along line 3—3 of FIG. 2;

FIG. 4 is an enlarged perspective view of the jaws supporting a tube/vessel;

FIG. 5 is a section view of the instrument taken along line 5—5 of FIG. 2; and

FIG. 6 is a section view of the instrument taken along line 6—6 of FIG. 5.

Detailed Description of the Drawings

A surgical instrument, according to the present invention, is shown in the drawings at 10. The instrument 10 is particularly suitable for the performance of laproscopic procedures, however its utility is not so limited. The instrument 10 consists of a control end at 12 and a forward working end at 14. During a laproscopic procedure, the working end 14 resides internally of a patient and the control end 12 is exposed for manipulation by the surgeon.

To perform a laproscopic procedure, a nail (not shown) surrounded by a sheath (not shown) is forced through the abdominal wall of the patient The nail is then removed to provide a passageway for the insertion of a surgical instrument, such as the instrument 10. It is desirable to minimize the size of the instrument and thereby the sheath required to facilitate its entry. By minimizing the sheath size, the opening in the abdominal wall is minimized with the result that rapid healing of the abdominal wound can occur.

The working end 14 of the instrument 10 consists of first and second jaws 16, 18, which are selectively movable towards and away from each other between a closed position, shown in FIG. 1, and an open position, shown in FIG. 2. The jaws 16, 18 are connected to an elongate stem 20 and project forwardly in cantilever fashion therefrom. Each of the jaws 16, 18 has a bowed configuration, as seen most clearly in FIG. 2.

Opening and closing of the jaws 16, 18 is effected by varying the relative lengthwise positions between the stem 20 and an elongate sleeve 22, which surrounds the stem 20 so as to guide relative lengthwise movement between the stem 20 and sleeve 22. By moving the stem 20 to the left in FIG. 2 relative to the sleeve 22, the bowed surfaces 24, 26 on the jaws 16, 18, respectively, are progressively squeezed within the sleeve opening 22 and towards each other until the closed instrument position of FIG. 1 is realized. The relative lengthwise movement between the stem 20 and sleeve 22 is effected by the mechanism at the instrument control end 12, as described in detail below.

It is desirable that the jaws 16, 18 have a substantial surface area to facilitate the performance of certain surgical procedures, as for example, the reversal of a tubal ligation. This procedure requires that the free ends of the severed fallopian tubes be held in close proximity to each other, stabilized and sutured Due to the flexible nature of the tubes, a substantial support surface is required on the instrument to stabilize each tube end to make the proper connection possible. It is conventional to provide instruments with wide jaw surfaces to facilitate performance of such a procedure. However, this necessitates the provision of a sheath of sufficient diameter to accept the wide jaws.

The present invention offers an alternative to the use of laproscopic instruments with a fixed configuration and wide jaws. To accomplish this end, arms 28, 30 are attached movably to the free ends 32, 34 of jaws 16, 18 respectively. Each of the arms 28, 30 has a flat, rectangular configuration, with flat surfaces 36, 38 that, with the jaws 16, 18 in their closed position, facially engage each other. The arm 28 is pivotally attached through a pin 40 to the free end 32 of the jaw 16 and the arm 30 is connected to the free end 34 of the arm 18 through a similar pin 42 so that the arms 28, 30 rotate about a single axis.

The movement of each arm 28, 30 with respect to its associated jaw 16, 18 is the same and this movement will be described herein with respect to one representative arm 28, as shown in FIGS. 3. The arm 28 is mounted to the jaw 16 for movement between entry and support positions. In the phantom, entry position in FIG. 3, the length of the arm 28 is aligned with the length of the stem 20 and jaw 16 to which it attaches, so that the working end 14 of the instrument 10 has a compact profile. The width W of the arm 28 is approximately equal to the width W' of the jaw 16. Accordingly, the diameter of the opening of the sleeve 22 need be only slightly larger than the dimension W' to permit sliding movement of the jaws 16, 18 within the opening through the sleeve 22, and in turn the diameter of the sheath through the abdominal wall need be only slightly larger than the sleeve diameter. The arm 28 is rotatable in a counterclockwise direction about pin 40 in FIG. 3 from the entry position to the solid line, support position. In the support position, an elongate edge 44 on the arm 28 is situated transversely of the length of jaw 16 and stem 20. Pivoting movement of the arm 28 between the entry and support positions in FIG. 3 is accomplished through a flexible rod 46, which is shifted relative to the sleeve 22 through the mechanism at the instrument control end 12, as described in detail below. Preferably, the arm 28 is rotatable by rod 46 through approximately 90° from its entry position, or through a slightly lesser angle, as shown in FIG. 3.

It can be seen in FIG. 4 that with the jaws 16, 18 closed and the arms 28, 30 abutting each other, an opening/space 48 is defined between the jaws 16, 18 to facilitate passage therethrough of a tube/vessel 50. In the support position of FIGS. 3 and 4, the arms 28, 30 are situated so that an elongate edge 52 on the arm 30 and the edge 44 on the arm 28 cooperatively provide a bearing surface for a flexible tube 50, such as a fallopian tube, extended through the opening 48 between the jaws 16, 18. A substantial length of the flexible tube 50 resting on the edges 44, 52 is thereby maintained in a straight orientation so that the free end 54 of the tube 50 is readily accessible to be connected to another tube end (not shown), held in like fashion by a like instrument 10.

The operation of the instrument 10 will now be described with respect to the control end 12 thereof. The control end 12 consists of a sleeve block 56, a pusher block 58 and a spring element 60 connected to the sleeve and pusher blocks 56, 58 so as to urge the blocks 56, 58 away from each other lengthwise of the instrument 10. The sleeve block 56 has a threaded bore 62 to accept a male fitting 64 fixedly attached to the control end 66 of the sleeve 22 so that the sleeve 22 can be removably fixedly attached to the sleeve block 56. The sleeve block 56 has a threaded bore 68 to accept a set screw 70 to fix the lengthwise position of the elongate stem 20 relative to the block 56 and sleeve 22.

The stem 20 is hollow and guidingly accepts an elongate core 72 for lengthwise relative movement therebetween. The rod 46 associated with the jaw 16 and a similar rod 74 associated with the jaw 18 are fixedly connected to the core 72 adjacent to the working end thereof. The rod 46 is connected to the arm 28 and the rod 74 connected to the arm 30 at locations 76, 78, respectively offset from the axes of the pins 40, 42. Forward movement of the core 72 relative to the sleeve 22 effects forward shifting of the rod 46 and resultingly pivoting movement of the arm 28 in a counterclockwise direction from the entry position to the support position in FIG. 3. The core 72 simultaneously shifts the rod 74 forwardly to effect a corresponding movement of the arm 30. Guide tubes 80, 82 are fixed to the inside of jaws 16, 18 respectively, to guidingly receive the rods 46, 74 respectively and maintain the rods 46, 72 in close proximity to their associated jaw 16, 18, to thereby prevent obstruction of the space 48 between the jaws 16, 18. Similar guide tubes 84, 86 are fixedly secured to the stem 20, adjacent the working end thereof.

A spring loaded fitting 88 is threadably attached to the free end 90 of the stem 20 and supports the pusher block 58. With the fitting 88 attached to the stem end 90, the free end 92 of the core 72 projects into a bore 94 through the fitting 88. The fitting 88 has an enlarged, disk-shaped head 96 and an integral, coaxial, cylindrical body 98 projecting rearwardly therefrom. The fitting 88 receives a trigger 100 having a body 102 guided for translatory movement within the fitting bore 94, a stem 106 for engagement with the free end 92 of the core 72 and a threaded free end 108 to accept a retention nut 110 at the control end 12 of the instrument 10. The trigger 100 is biased by a coil spring 112 compressed lengthwise between a rearwardly facing annular shoulder 114 on the fitting 88 and a forwardly facing annular shoulder 116 on a radially enlarged bead 118 on the trigger 100. The nut 110 prevents the pusher block 58 from sliding rearwardly off of the fitting 88.

In a normal condition, the spring 60 forces the pusher block 58 away from the sleeve block 56. The rear edge 120 of the pusher block 58 bears against the retention nut 110 under the force of spring 60 to draw the end 108 of the trigger 100 rearwardly so that a rearwardly facing annular shoulder 122 abuts a forwardly facing shoulder 124 at the control end of the fitting 88. The shoulder 122 urges the fitting 88 rearwardly, thereby drawing with it the attached stem 20. In this position, the sleeve 22 surrounds a portion of the jaws 16, 18 so that the jaws 16, 18 are closed.

The jaws 16, 18 are opened from the FIG. 1 position by moving the pusher block 58 forwardly relative to the sleeve block 56. To facilitate this movement, oppositely projecting finger grips 126, 128 are provided on the sleeve block 56. The user grasps the grips 126, 128 with two fingers in the same manner as a syringe is grasped and with the thumb presses on the free end 130 of the instrument 10. By so doing, the pusher block 58, trigger 100 and nut 110 are moved forwardly as a unit. The spring 112 transmits the forward operating force from the trigger 100 to the fitting 88, which in turn shifts the attached stem 20 forwardly relative to the sleeve 22 so that the jaws 16, 18 are exposed at the free end 132 of the sleeve 22. Because the jaws 16, 18 are normally biased away from each other, once they are unconfined by the sleeve 22, the jaws 16, 18 spread apart. Forward movement of the fitting 88 and stem 20 continues until the leading face 134 of the fitting 88 abuts the rearwardly facing surface 136 of the sleeve block 56.

The resistant force of spring 112 is greater than that of spring 60 so that as the biasing force of spring 60 is overcome by forward movement of the pusher block 58 relative to the sleeve block 56, the movement of block 58 is transmitted through the spring 112 as a corresponding movement of the fitting 88 and stem 20. Upon the fitting 88 encountering the block 56 with forward pressure being applied to the instrument end 130, the force of spring 112 is overcome, thereby moving the trigger 100 forwardly relative to the block 58 and fitting 88 to the position shown in FIG. 5, wherein a shoulder 138 on the trigger abuts the free end 140 of the fitting 88 so that further trigger movement is arrested. As the force of spring 112 is overcome, the forwardly moving trigger 100, through the stem 106, urges the core 72 forwardly relative to the sleeve 22 and thereby forces the rods 46, 74 forwardly to effect pivoting of the arms 28, 30 from their entry to their support positions.

To maintain the arms 28, 30 in their support positions, with the control end 12 of the surgical instrument 10 in the FIG. 5 position, a detent mechanism 142 is provided on the block 58. The fitting 88 has an annular recess 144 which is designed to cooperate with a metal ball 146 on the detent mechanism 142. The ball 146 is biased into the recess 144 by an actuator 148. The actuator 148 has an enlarged head 150 to facilitate its manipulation, and an integral post 152 biased by a coil spring 154 radially inwardly against the ball 146. With the arms 28, 30 in their support positions, the ball 146 is driven into the recess 144 on the fitting 88 to thereby prevent lengthwise shifting of the fitting 88 relative to the block 58. By drawing up on the actuator head 150 against the spring 154, the ball 146 can be wedged out of the recess 144 to thereby release the fitting 88 from the block 58.

The foregoing disclosure of specific embodiments is intended to be illustrative of the broad concepts comprehended by the invention.

I claim:

1. A surgical instrument for performing a laproscopic procedure, said instrument comprising:

an elongate stem having first and second jaws that are selectively movable towards and away from each other into closed and open positions respectively;

an arm having an elongate edge;

means for mounting the arm to one of said first and second jaws for movement between (a) a first position wherein the length of the edge is aligned lengthwise of said elongate stem and (b) a second position wherein the length of the edge is transverse to the position that said edge assumes, with the arm in its first position; and means operable from a position remote from said arms for manually moving said arm selectively between said first and second positions.

2. The surgical instrument according to claim 1 wherein means are provided on at least one of the jaws for defining an opening between the jaws with the jaws in their closed position.

3. The surgical instrument according to claim 1 wherein the arm mounting means comprises means for pivotably mounting the arm to said one of said first and second jaws.

4. The surgical instrument according to claim 1 wherein there is a second arm and means for mounting the second arm to the other of the first and second jaws for movement between (a) a first position wherein the length of the second arm edge is aligned lengthwise of said elongate stem and (b) a second position wherein the length of the second arm edge is transverse to the position that said second arm edge assumes with the second arm in its first position and the moving means simultaneously moves the first claimed arm and second arm between their first and second positions.

5. The surgical instrument according to claim 1 wherein at least one of said jaws has a bowed configuration, said jaws are normally biased away from each other, an elongate sleeve is provided for surrounding the stem and at least a portion of said jaws, and means are provided for effecting lengthwise relative movement between the elongate sleeve and stem, said sleeve being dimensioned so that upon the sleeve surrounding at least a portion of the bowed jaw said jaws are squeezed by said sleeve towards their closed positions.

6. The surgical instrument according to claim 1 wherein means are provided for releasably maintaining the arm in said second position 7. The surgical instrument according to claim 5 wherein means are provided for normally biasing the stem to a position wherein at least a portion of the bowed jaw is within the sleeve so that the jaws tend towards their closed position.

8. The surgical instrument according to claim 5 wherein means are provided for fixing the relative lengthwise positions of said sleeve and stem so that the jaws can be maintained in each of said open and closed positions.

9. A surgical instrument for performing a laproscopic procedure, said instrument comprising:

an elongate item having first and second jaws that are selectively movable towards and away from each other into closed and open positions respectively;

first and second arms each having an elongate edge;

means for mounting the first arm to the first jaw and the second arm to the second jaw for pivoting movement of each of said arms relative to its respective jaw between (a) a first position wherein the length of the edge is aligned lengthwise of said elongate stem and (b) a second position wherein the length of the edge is transverse to the position that the edge assumes with the arm associated with the edge in its first position; and means operable from a position remote from said arms for simultaneously manually moving said arms selectively between their first and second positions.

10. The surgical instrument according to claim 9 wherein each said jaw has a bowed configuration, an elongate sleeve is provided and surrounds said stem so as to guide lengthwise relative movement between said sleeve and stem and with said sleeve situated relative to said stem so as to surround at least a portion of said jaws the jaws are squeezed by said sleeve towards each other and their closed position.

11. The surgical instrument according to claim 9 wherein means are provided on at least one of the jaws for defining an opening between the jaws with the jaws in their closed position.

12. The surgical instrument according to claim 9 wherein said first and second jaws are normally biased away from each other into said open position.

13. The surgical instrument according to claim 9 wherein means are provided for releasably maintaining each of the jaws in its second position 14. A surgical instrument for performing a laproscopic procedure, said instrument comprising:

an elongate stem having first and second jaws that are selectively movable towards and away from each other into closed and open positions respectively;

first and second arms each having an elongate edge;

means for mounting the first arm to the first jaw and the second arm to the second jaw for pivoting movement of each of said arms relative to its respective jaw between (a) a first position wherein the length of the edge is aligned lengthwise of said elongate stem and (b) a second position wherein the length of th edge is transverse to the position that the edge assumes with the arm associated with the edge in its first position; and means for simultaneously manually moving said arms selectively between their first and second positions, wherein each jaw has a bowed configuration, an elongate sleeve is provided and surrounds said stem so as to guide lengthwise relative movement between said sleeve and stem and with said sleeve situated relative to said stem so as to surround at least a portion of said jaws the jaws are squeezed by said sleeve towards each other and their closed position, wherein said means for manually moving the arms comprises first and second rods, means for mounting the rods within the sleeve for lengthwise movement relative to the sleeve, and means for mounting the first rod to the first arm and the second rod to the second arm so that lengthwise movement of the rods imparts pivoting movement to the arms between their first and second positions.

15. A surgical instrument for performing a laproscopic procedure, said instrument comprising:

an elongate stem having first and second jaws that are selectively movable towards and away from each other into closed and open positions respectively, each said jaw having a bowed portion and said jaws being normally biased away from each other towards its open position;

first and second arms each having an elongate edge;

means for mounting the first arm to the first jaw and the second arm to the second jaw for pivoting movement of each of aid arms relative to its respective jaw between (a) a first position wherein the length of the edge is aligned lengthwise of said elongate stem and (b) a second position wherein the length of the second arm edge is transverse to the position that said edge assumes with its associated arm in its first position;

an elongate sleeve surrounding said stem so as to guide relative lengthwise movement between said sleeve and elongate stem, said sleeve being movable lengthwise of said stem into surrounding relationship with said bowed jaw portions to thereby squeeze the jaws towards each other into their closed position;

first and second rods mounted within said sleeve;

means for attaching the first and second rods to the first and second arms respectively;

means for moving the rods lengthwise relative to the sleeve and for thereby effecting simultaneous pivoting movement of the arms between the first and second arm positions;

means for releasably fixing the relative positions of the sleeve and stem; and means for releasably maintaining the first and second arms in each of their first and second positions.

16. The surgical instrument according to claim 15 including a sleeve block to which the sleeve is fixedly mounted, a pusher block, means for connecting the pusher block to the stem, and means for biasing the pusher block away from the sleeve block and thereby the stem relative to the sleeve in such a manner that the sleeve is urged into surrounding relationship with the bowed jaw portions to thereby urge the jaws towards their closed position.

17. The surgical instrument according to claim 16 wherein means are provided for biasing the rods relative to the sleeve to situate the arms in their first position and cooperating means are provided on the sleeve block, pusher block and rod biasing means for moving the rods relative to the sleeve to thereby move the arms from their first position to their second position upon the pusher block being moved towards the sleeve block.

18. The surgical instrument according to claim 17 wherein spaced finger grips are provided in the sleeve block to facilitate holding and operation of the instrument.

19. The surgical instrument according to claim 17 including means for releasably maintaining the arms in their second positions.

* * * * *